United States Patent [19]

Stille

[11] 4,259,519

[45] Mar. 31, 1981

[54] PROCESS FOR THE CARBONYLATION OF DIOLEFINS

[75] Inventor: John K. Stille, Fort Collins, Colo.

[73] Assignee: Polymer Sciences Corporation, New York, N.Y.

[21] Appl. No.: 926,132

[22] Filed: Jul. 19, 1978

Related U.S. Application Data

[63] Continuation-in-part of Ser. No. 591,120, Jun. 27, 1975, abandoned.

[51] Int. Cl.³ .............................................. C07C 67/38
[52] U.S. Cl. .................................... 560/193; 560/81; 560/183; 560/198; 560/204; 560/206; 562/483; 562/590; 562/592; 562/595
[58] Field of Search ................... 560/204, 193, 81; 562/522, 590, 592, 595, 483

[56] References Cited

U.S. PATENT DOCUMENTS

| | | | |
|---|---|---|---|
| 3,397,226 | 8/1968 | Fenton | 560/204 |
| 4,171,450 | 10/1979 | Kesling et al. | 560/204 |

FOREIGN PATENT DOCUMENTS 130714 10/1975 Japan ...................................... 560/204

OTHER PUBLICATIONS

Carraro et al., Ger Offen. 1904429 as cited in Chem. Abstracts, 72, 12118u, (1970).
Pylander, *Organic Syntheses with Noble Meta Catalysts*, pp. 233-236 (1973).
James et al., JACS, 98:7, pp. 1810-1823 (1976).
Stille et al., J. Org. Chem. 44, 3474-3482 (1979).
James, as cited in Chem. Abstracts, 83, 205679p (12/22/75).

*Primary Examiner*—Jane S. Myers
*Attorney, Agent, or Firm*—Pennie & Edmonds

[57] ABSTRACT

Conjugated diolefins (e.g., 1,3-butadiene) are carbonylated by the palladium-catalyzed addition of carbon monoxide and an alcohol of the formula ROH (e.g., benzyl alcohol) whereby polycarboxylic esters are formed in which the pair of double bonds of the conjugated diolefin has been transformed into a moiety having the formula:

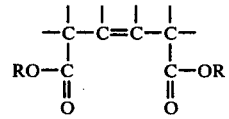

In the process, the olefin, carbon monoxide, and alcohol are reacted in the presence of a palladium(II) salt, a copper(II) salt, and a base, at certain concentrations and at a pressure and temperature sufficient to effect the carbonylation. The resulting unsaturated diester can be hydrolyzed and hydrogenated or vice versa to obtain the corresponding linear diacid (e.g., adipic acid).

21 Claims, No Drawings

PROCESS FOR THE CARBONYLATION OF DIOLEFINS

CROSS-REFERENCE TO RELATED APPLICATION

This is a continuation-in-part of Ser. No. 591,120 filed June 27, 1975, now abandoned.

BACKGROUND OF THE INVENTION

This invention relates to the carbonylation of diolefins. More particularly, it relates to the catalytic carbonylation of diolefins to form esters of polycarboxylic acids under exceptionally mild conditions of temperature and pressure.

A petrochemical process of major economic importance is the conversion of unsaturated hydrocarbons to functionally substituted products such as alcohols, aldehydes, ketones, and carboxylic acids. The hydroformylation of olefins to aldehydes is one such process, and is the first step in the synthesis of oxo alcohols. However, the energy requirements for the oxo process are severe, temperatures above 150° C. and pressures of up to 3000 p.s.i.g. usually being necessary.

The addition of carbon monoxide to olefins (carbonylation) has long been considered in the art to be a highly attractive route to a number of commercially valuable chemical products. In particular, there has been a long-felt need for a convenient method of adding carboxyl groups across a pair of conjugated double bonds in a 1,4-manner efficiently yet under mild conditions of temperature and pressure to form the corresponding $\Delta^3$-adipic acid derivative. A recent survey of prior work in this field appears in Advances in Chemistry, No. 132, "Homogeneous CatalysisII" (American Chemical Society 1974). For example, a facile 1,4-dicarbonylation of butadiene to form an adipic acid precursor would be valuable in the commercial production of linear polyesters and polyamides.

The reaction of carbon monoxide with a variety of cyclic and acyclic olefins at 2-3 atm in methanol in the presence of palladium(II) chloride as catalyst and copper(II) chloride as reoxidant to give, depending on the reaction conditions, various carboxylic acid derivatives, is disclosed in Advances in Chemistry, supra, p.90; J. Am. Chem. Soc., 98, 1810 (1976) and J. Org. Chem., 41, 1504 (1976). For example, linear alpha-olefins give predominantly beta-methoxyesters by trans-addition under neutral conditions and succinic esters by cis-addition in the presence of base:

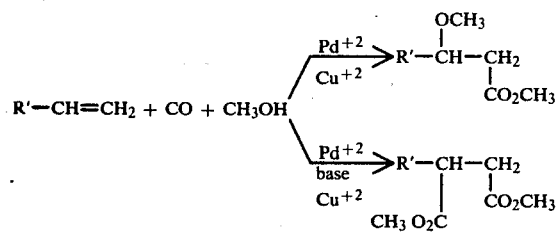

In the synthesis of the above-mentioned beta-methoxyester, a trans-solvopalladation reaction of the olefin is believed to be the first step in the mechanism, followed by carbon monoxide insertions into the metal-palladium sigma bond, as described in J. Am. Chem. Soc., 95, 5062 (1973); J. Am. Chem. Soc., 98, 1806 (1976); J. Am. Chem. Soc., 97, 3282 (1965); J. Am. Chem. Soc., 88, 5135 (1966); J. Am. Chem. Soc., 92, 1274 (1970); J. Am. Chem. Soc., 92, 1798 (1972); J. Am. Chem. Soc., 94, 485 (1972); and Inorg. Nucl. Chem. Letters, 5, 157 (1969). Other reaction solvents with or without added nucleophiles afford beta-substituted carboxylic acid derivatives by the same mechanistic sequence, as described in "Transition Metal Catalyzed Carbonylation of Olefins", Chapter 12 in "The Chemistry of Functional Groups. Supplement A: Double-Bond Functional Groups", S. Patai, Ed. (John Wiley and Sons, Inc., London, 1976). Such solvents (SOH) include alcohols, water, and acetic acid or non-reactive media; nucleophiles ($N^-$) include chloride, acetate, amines and the like:

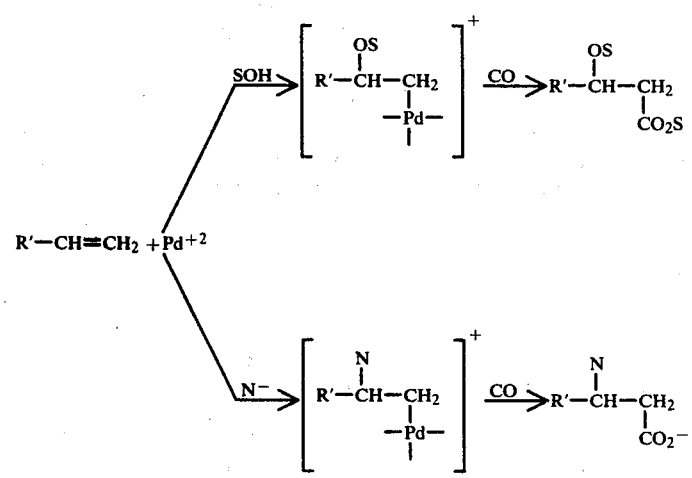

For example, cyclooctadiene can be catalytically converted, stereo-specifically, to the trans-beta lactone, as described in J. Am. Chem. Soc., 97, 674 (1975); and J. Organometal. Chem., 108, 401 (1976). It is especially noteworthy that this unique transformation to a strained, difficult-to-synthesize class of compounds can be effected at 25° C., under 1-3 atm of carbon monoxide from cheap starting materials:

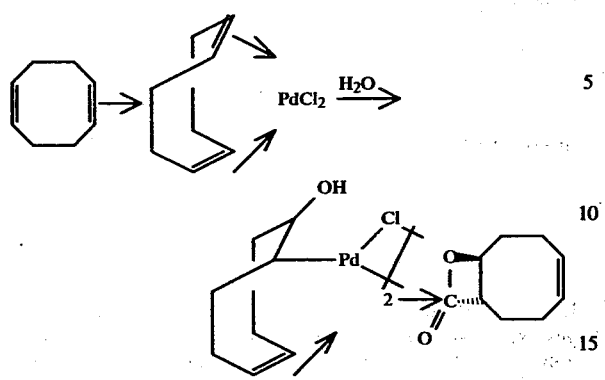

However, of greater importance as a petrochemical process is the reaction of carbon monoxide with conjugated olefins whereby the product obtained is the result of 1,4-addition of two carboxyl groups across a pair of double bonds. Of major technological significance would be the ability to carry out such processes under mild energy and pressure requirements to form dicarboxylic acid derivatives, e.g. esters.

Accordingly, it is an object of the present invention to provide a process for the carbonylation of olefins to form derivatives of polycarboxylic acids.

Another object is to provide a process for the carbonylation of conjugated diolefins under mild conditions of temperature and pressure to form esters of dicarboxylic acids.

These and other objects as well as a fuller understanding of the invention and the advantages thereof can be had by reference to the following description and claims.

SUMMARY OF THE INVENTION

The foregoing objects are achieved according to the present invention whereby it has been discovered that diolefins having conjugated double bonds of the formula

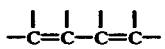

are converted, by the palladium-catalyzed addition to said double bond of carbon monoxide and an aliphatic alcohol of the formula ROH, to dicarboxylic esters in which the conjugated double bonds have been transformed by 1,4-dicarbonylation into a moiety having the formula:

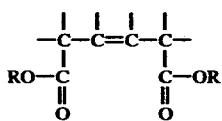

wherein R is an aralkyl or saturated alkyl group. The process comprises charging the olefin and alcohol together with a palladium(II) salt, a copper(II) salt and a carefully controlled amount of base to a reaction vessel and subjecting the contents of the charged vessel, in the absence of water and oxygen, to a carbon monoxide pressure and a temperature sufficient to effect the carbonylation reaction. In the specific case of a conjugated diolefin of the formula R'—CH=CH—CH=CH—R" wherein R' and R" are each independently hydrogen or saturated alkyl, the carbonylation reaction can be represented by the following equation:

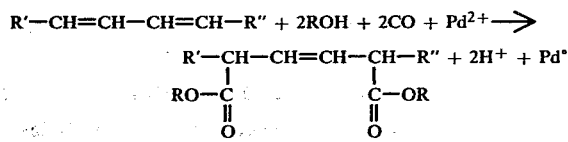

Diolefins suitable for use in the present invention are conjugated diolefins such as butadiene and isoprene.

The alcohol, ROH, can be an aliphatic alcohol, such as methanol and ethanol or, preferably, an aralkyl alcohol, such as benzyl alcohol. In addition, polyols such as diols can be used, in which case the product of the carbonylation may be a polyester. Thus, when conjugated diolefins are dicarbonylated using a dihydric alcohol, linear polyesters are formed. With appropriate control of the reaction conditions, such linear polyesters will have molecular weights high enough to permit the spinning of useful fibers.

The carbon monoxide pressure can vary over a wide range, but is introduced conveniently at from 1 to 15 atm, preferably 1 to 3 atm, and in a quantity sufficient to complete the dicarbonylation of the conjugated double bond system. A wide range of relatively mild temperatures, i.e., 20°–100° C., can also be employed; however, room temperature, i.e., 25° C., is generally the most convenient. It is therefore an important feature of the present invention that the carbonylation reaction can be carried out under combined conditions of temperature and pressure which would be considered unusually mild compared to previously known carbonylation reactions. Thus, the process lends itself to the utilization of starting materials and the synthesis of polycarboxylic esters which might otherwise be too sensitive to use or produce by other means.

The palladium(II) and copper(II) compounds suitable for use in the present invention include a wide variety of salts of divalent palladium and copper, although palladium(II) halides and copper(II) halides are preferred, with palladium(II) chloride (palladium dichloride) and copper(II) chloride (cupric chloride) being especially preferred.

The purpose of the copper(II) salt is to reoxidize the palladium from Pd° back to its active +2 oxidation state. Thus, for each dicarbonylation, palladium(II) is reduced during the reaction to Pd°. The latter is then reoxidized by Cu(II) back to Pd(II), the Cu(II) salt being reduced to Cu(I) according to the following equation:

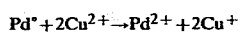

In this way the Pd(II) can be used in the carbonylation and turned over as many times as necessary provided the equivalent amount or more of Cu(II) is present. It is possible, at the end of the reaction, to regenerate the Cu(II) by oxidation with air or oxygen. Thus, enough copper is necessary only for the completion of a given batch; following the removal of the organic products, the copper-palladium salt mixture can be regenerated with air or oxygen. More olefin can then be added and a new batch started.

An important feature of the carbonylation process of the invention is the discovery that anaerobic conditions together with a controlled amount of nucleophilic base greatly improve the yield of the desired product, especially in the case of open-chain diolefins. In particular, the process of the invention is carried out using a molar amount of base equal to or greater than the molar amount of copper(II) reoxidant. Preferably, 2 molar equivalents of base are employed per mole of copper(II) reoxidant. The preferred bases are alkali and alkaline earth metal salts of carboxylic acids, e.g., sodium acetate, potassium acetate, sodium propionate, sodium butyrate, and the like. Other bases can be used, including a wide variety of acid scavengers such as amines (e.g., triethyl amine, lutidine) and carbonates (e.g., sodium carbonate).

As indicated above, conjugated diolefins in the presence of added base, catalytic amounts of palladium(II) chloride and a stoichiometric amount of copper(II) chloride at 1–3 atm of carbon monoxide afford unsaturated diesters. For example, butadiene yields esters of 3-hexenedioic acid. ($\Delta^3$-adipic acid):

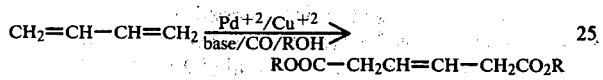

These products are particularly useful as intermediates for making commercially valuable adipic acid and derivatives thereof.

The course of the reaction of 1,3-butadiene with carbon monoxide (3 atm) in methyl or benzyl alcohol and in the presence of catalytic amounts of palladium(II) chloride has been discovered to be particularly sensitive to the amount of added base. For example, using less than a molar amount of sodium butyrate per molar amount of cupric chloride employed produces the 5-chloropent-3-eneoate and 5-methoxypent-3-eneoate in addition to the desired 3-hexenedioate. However, using one or more and preferably two molar equivalents of sodium butyrate per mole of cupric chloride gives only the desired adipic acid derivative in greater than 80% conversion.

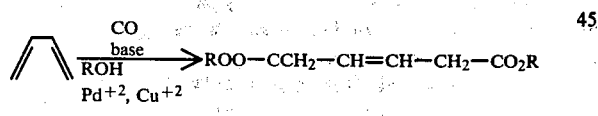

In a preferred mode of carrying out the present process, the reaction of 1,3-butadiene with carbon monoxide in benzyl alcohol in the presence of catalytic amounts of palladium(II) chloride, stoichiometric amounts of copper(II) chloride as a reoxidant and sodium butyrate as base yields dibenzyl trans-hex-3-ene-1,6-dioate (dibenzyl trans-$\Delta^3$-adipate) in 91% conversion.

Without wishing to be bound by theory, it is believed that the mechanism of the reaction using benzyl alcohol involves the intermediate carbobenzyloxy palladium complex(1) which undergoes 1,4-insertion via the σ-bonded complex or the π-allyl complex (2) as shown in the following reaction scheme. The stereochemistry of carbomethoxy palladation is cis where the carbomethoxy group and palladium add cis across the double bond in an olefin. Carbonyl insertion followed by alcoholysis yields the dibenzyl-hex-3-ene-1,6-dioate. It is not clear if the cis ester, the expected product from the allyl complex, is formed first and then undergoes isomerization

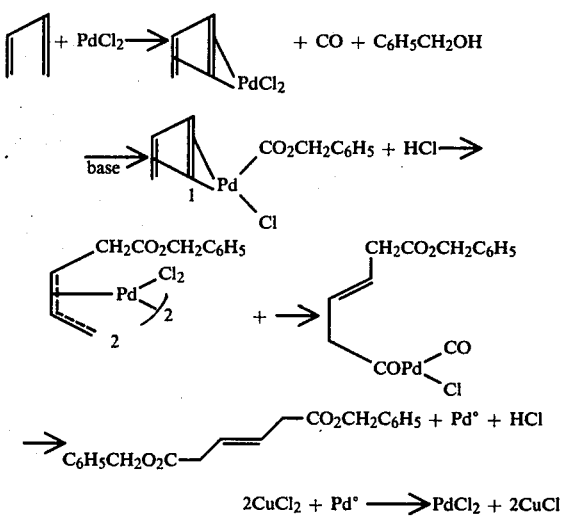

to the more stable trans isomer. The latter isomer would be favored in this case because of the introduction of the two bulky benzyl groups.

The structure of the trans-diester can be verified by an independent synthesis from trans-hex-3-ene-1,6-dioic acid and benzyl alcohol and also by hydrolysis of the reaction product to trans-hex-3-ene-1,6-dioic acid.

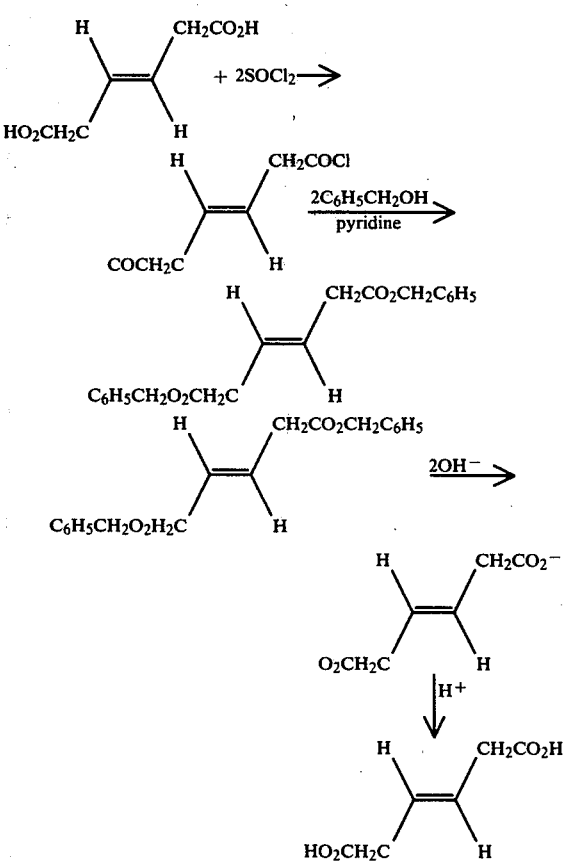

DESCRIPTION OF PREFERRED EMBODIMENTS

The following examples are presented for the purpose of illustrating, without limitation, the carbonylation process of the present invention and the advantages thereof.

The carbonylation reactions are carried out using a modified Paar series 3910 hydrogenation apparatus in 250 ml or 500 ml heavy-walled Pyrex serum or pressure bottles. Alternatively, a 200 ml heavy-walled Pyrex serum or pressure bottle containing the reaction mixture and fitted with a neoprene septum can be used. The atmosphere in the bottle is flushed with carbon monoxide several times after pressurizing to ensure complete removal of air. The carbon monoxide is introduced through a needle valve clamped securely into the pressure tubing leading from a ballast tank. In this configuration, the atmosphere above the reaction and/or the reaction mixture itself can be sampled using the appropriate capacity gas-tight syringe fitted with, e.g., a Hamilton inert #1FM1 two-way valve and a needle. The needle is inserted through the septum with the valve closed, and by careful opening, the aliquot is drawn into the syringe. The valve is then closed and the device withdrawn from the bottle. In this manner, the gas or liquid under pressure can be removed from the reaction vessel with little loss of sample.

EXAMPLE I

Dicarbonylation of 1,3-Butadiene in Benzyl Alcohol

To a solution of 20.2 grams (150 mmoles) of anhydrous copper(II) chloride in 75 ml of benzyl alcohol in a pressure bottle are added 16.5 grams (150 mmoles) of anhydrous sodium butyrate, 3.0 grams (30 mmoles) of trimethylorthoformate, and 0.20 gram (1.12 mmoles) of palladium(II) chloride. The reaction mixture is cooled in a dry ice-isopropanol slush and 1.26 grams (34.4 mmoles) of butadiene are transferred into the pressure bottle. The mixture is pressurized with 3 atm of carbon monoxide and heated to 60° C. in an oil bath. No further carbon monoxide uptake is observed after 144 hrs at which point the reaction mixture is black.

The reaction mixture is poured into 100 ml of water and extracted four times each with 150 ml of chloroform. The combined extracts are dried over anhydrous sodium sulfate and concentrated under reduced pressure. The benzyl alcohol is distilled off at 90° C./10 mm pressure and the residual oily liquid (3.22 grams; 91% conversion) is analyzed by gas chromatography and identified as dibenzyltrans-hex-3-ene-1,6-dioate. The structure of the product is further confirmed by the following analytical data: I.R. 3100 cm$^{-1}$ (aromatic stretch);

1735 cm$^{-1}$ (—C);
‖
O 1140 cm$^{-1}$ (—C—O); 900 cm$^{-1}$, 675 cm$^{-1}$ (C—H bending); 1H nmr CDCl$_3$ δ7.2–7.4 (m,SH aromatic) δ6.4–6.8 ppm (m, 1H vinylic) δ3.9 ppm (S, 2H—OCH$_2$), δ2.0–2.4 ppm (m, 2H, CH$_2$) $^{13}$C nmr 171.616 (—C),
‖
O 138.887, 126.607, 125,268, 124.960, 124.087 (aromatic and olefinic) 63.542 (—OCH$_2$) 48.845 (methylene) Anal. Calcd for C$_{20}$H$_{20}$O$_4$: C, 74.04; H, 6.74. Found: C, 73.76; H, 7.06.

Additional confirmation of the structure of the product is obtained by independent synthesis of dibenzyl-trans-hex-3-ene-1,6-dioate whereby a mixture of 3.0 grams (20.8 mmole) of trans-hex-3-ene-1,6-dioic acid and 30 ml of thionyl chloride are heated to reflux for 2 hours on a steam bath. At the end of this time the excess thionyl chloride is removed by distillation (79° C.) and the resulting oil is treated with 5.0 grams (45 mmole) of freshly distilled benzyl alcohol and 4.0 grams (50 mmole) of pyridine. The mixture is then heated to 100° C. for 4 hours and poured into 100 ml of water and extracted twice each with 50 ml of ether. The ether extract is washed with dilute sodium bicarbonate solution. After drying over anhydrous sodium sulfate the ether is concentrated under reduced pressure. The excess benzyl alcohol is removed by distillation (90° C./10 mm) to yield a residual oily liquid (4.2 grams) of dibenzyl-trans-hex-3-ene-1,6-dioate which is identical to the reaction product obtained from the carbonylation of 1,3-butadiene.

Hydrolysis of Dibenzyl-Trans-Hex-3-Ene 1,6-Dioate

A suspension of 1.62 grams (5.00 mmoles) of dibenzyl-trans-hex-3-ene-1,6-dioate in 25 ml of 10% sodium hydroxide solution is heated to reflux for 12 hours. At the end of this time the reaction mixture is cooled and extracted twice, each with 15 ml of chloroform. The aqueous phase is acidified with dilute hydrochloric acid and extracted three times with 50 ml portions of ether. The ether extracts are combined, dried over anhydrous sodium sulfate and concentrated under reduced pressure. Recrystallization of the yellowish residual oil from aqueous methanol yields 0.25 gram of trans-hex-3-ene-1,6-dioic acid, m.p.=197°–198° C. (Lit. m.p.=199°). The melting point of a mixture of the reaction product and an authentic sample obtained from Aldrich Chemical Co. remains unchanged.

The unsaturated dioic acid can be hydrogenated to adipic acid using any of a variety of catalysts of reducing agents well known to those skilled in organic chemistry to selectively reduce the olefinic double bond without disturbing the terminal carboxyl groups. Such catalysts and reagents include, for example, palladium hydroxide on carbon and diimide as described in Fieser et al., *Advanced Organic Chemistry*, p. 180 (Reinhold, 1961); and *J. Chem. Ed.*, 42, 254 (1965). Alternatively, the lability of the benzyl ester functional groups toward catalytic hydrogenolysis can be taken advantage of so as to provide a one-step conversion of dibenzyl-trans-hex-3-ene-1,6-dioate to adipic acid using the appropriate hydrogenolysis/hydrogenation catalyst, e.g., palladium oxide or hydroxide on carbon.

EXAMPLE II

Dicarbonylation of 1,3-Butadiene in Methanol

A mixture of 75 ml anhydrous methanol, 13.44 grams (100 mmoles) copper(II) chloride, 11.0 grams or 22.0 grams (100 or 200 mmoles) of sodium butyrate and 3.0 ml (18 mmoles) of trimethyl orthoformate in a 250 ml pressure bottle was connected to the carbonylation apparatus. The mixture was cooled in a dry ice-isopropanol bath for 1 hour and then subjected to vacuum. In a separate apparatus, butadiene was condensed in a Schlenk tube cooled in a dry ice-isopropanol bath. The Schlenk tube was then connected to the pressure bottle (which was under reduced pressure) and allowed to warm up. The butadiene was allowed to condense into the well-cooled pressure bottle until the requisite amount of butadiene (25 mmoles) had passed over. The pressure in the system was then equalized by introducing a stream of nitrogen. Palladium(II) chloride (0.50 grams; 2.8 mmoles) was then introduced into the cold reaction mixture and the system was pressurized with 3 atm of carbon monoxide. The reaction was allowed to proceed at room temperature until the precipitation of palladium(0) was complete. The reaction mixture was then filtered and the residue washed with several portions of methanol. The combined filtrates were distilled until about 30 ml of solution was left. The methanol solution was subjected to continuous extraction with pentane for 48 hours. The pentane was then distilled using a Vigreux column, and the residual liquid dimethyl-trans-hex-3-ene-1,6-dioate was purified by distillation on a Kugelrohr apparatus.

Hydrolysis of the diester to trans-hex-3-ene dioic acid and subsequent hydrogenation to adipic acid can be achieved as indicated in the preceding example.

It will be understood that changes and variations in the foregoing examples can be made without departing from the scope of the invention which is defined in the following claims.

I claim:

1. In the conversion of olefins to carboxylic esters whereby a conjugated diolefin having the formula:

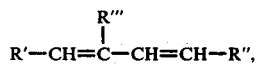

wherein R' and R" are each independently H, saturated alkyl, or aryl and R''' is H or methyl, is carbonylated, by the 1,4-addition thereto of carbon monoxide and an alcohol of the formula ROH, to form an unsaturated dicarboxylic ester having the formula:

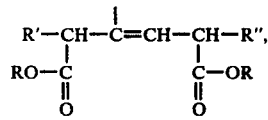

wherein R is aralkyl or saturated alkyl, the improvement comprising charging to a reaction vessel the diolefin, a copper(II) salt, a nucleophilic base selected from the group consisting of amines, carbonates, and alkali and alkaline earth metal salts of carboxylic acids, a catalytically effective amount of a palladium(II) salt, and amounts of carbon monoxide and alcohol equal to or greater than the stoichiometric equivalent of diolefin, and subjecting the contents of the charged vessel in the absence of water and oxygen to a carbon monoxide pressure and a temperature sufficient to effect the carbonylation reaction, said process being further characterized in that the amount of copper(II) salt employed is at least sufficient to substantially oxidize the palladium(0) formed in the process back to palladium(II) and the amount of base employed is equal to at least 1 molar equivalent of copper(II) salt.

2. The improvement according to claim 1 wherein the conjugated diolefin is butadiene.

3. The improvement according to claim 2 wherein the alcohol is benzyl alcohol.

4. The improvement according to claim 2 wherein the alcohol is methanol.

5. The improvement according to claim 2 wherein the alcohol is ethanol.

6. The improvement according to claim 1, 2, 3, 4, or 5 wherein:
   the carbon monoxide pressure is initially between about 1 and 15 atmospheres:
   the temperature is between about 20° and 100° C.;
   the palladium(II) salt is palladium dichloride;
   the copper(II) salt is cupric chloride; and
   the nucleophilic base is an alkali or alkaline earth metal salt of a carboxylic acid, said base being employed in an amount corresponding to between about 1 and 4 molar equivalents of copper(II) salt.

7. In the conversion of olefins to carboxylic acids whereby a conjugated diolefin having the formula:

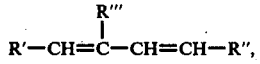

wherein R' and R" are each independently H, saturated alkyl, or aryl and R''' is H or methyl, is carbonylated, by 1,4-addition thereto of carbon monoxide and an alcohol of the formula ROH, to form an unsaturated dicarboxylic ester having the formula:

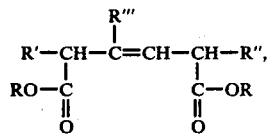

wherein R is aralkyl or saturated alkyl, and said diester is then hydrolyzed to form the corresponding unsaturated dicarboxylic acid, the improvement comprising charging to a reaction vessel the diolefin, a copper (II) salt, a nucleophilic base selected from the group consisting of amines, carbonates, and alkali and alkaline earth metal salts of carboxylic acids, a catalytically effective amount of palladium(II) salt, and amounts of carbon monoxide and alcohol equal to or greater than the stoichiometric equivalent of diolefin, and subjecting the contents of the charged vessel in the absence of water and oxygen to a carbon monoxide pressure and a temperature sufficient to effect the carbonylation reaction, said process being further characterized in that the amount of copper(II) salt employed is at least sufficient to oxidize the palladium(0) formed in the process back to palladium(II) and the amount of base employed is equal to at least 1 molar equivalent of copper(II) salt.

8. The improvement according to claim 7 wherein the conjugated diolefin is butadiene.

9. The improvement according to claim 8 wherein the alcohol is benzyl alcohol.

10. The improvement according to claim 8 wherein the alcohol is methanol.

11. The improvement according to claim 8 wherein the alcohol is ethanol.

12. The improvement according to claim 7, 8, 9, 10, or 11 wherein:
the carbon monoxide pressure is initially between about 1 and 15 atmospheres;
the temperature is between about 20° and 100° C.;
the palladium(II) salt is palladium dichloride;
the copper(II) salt is cupric chloride; and
the nucleophilic base is an alkali or alkaline earth metal salt of a carboxylic acid, said base being employed in an amount corresponding to between about 1 and 4 molar equivalents of copper(II) salt.

13. In the conversion of olefins to carboxylic acids whereby a conjugated diolefin having the formula:

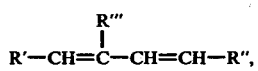

wherein R' and R" are each independently H, saturated alkyl, or aryl and R''' is H or methyl, is carbonylated, by 1,4-addition thereto of carbon monoxide and an alcohol of the formula ROH, to form an unsaturated dicarboxylic ester having the formula:

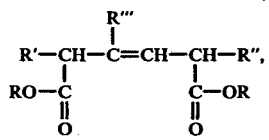

wherein R is aralkyl or saturated alkyl, and said diester is then hydrolyzed and hydrogenated to form a dicarboxylic acid having the formula:

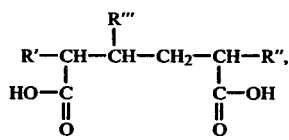

the improvement comprising charging to a reaction vessel the diolefin, a copper(II) salt, a nucleophilic base selected from the group consisting of amines, carbonates, and alkali and alkaline earth metal salts of carboxylic acids, a catalytically effective amount of a palladium(II) salt, and amounts of carbon monoxide and alcohol equal to or greater than the stoichiometric equivalent of diolefin, and subjecting the contents of the charged vessel in the absence of water and oxygen to a carbon monoxide pressure and a temperature sufficient to effect the carbonylation reaction, said process being further characterized in that the amount of copper(II) salt employed is at least sufficient to substantially oxidize the palladium(0) formed in the process back to palladium(II) and the amount of base employed is equal to at least 1 molar equivalent of copper(II) salt.

14. The improvement according to claim 13 wherein the conjugated diolefin is butadiene and the dicarboxylic acid is adipic acid.

15. The improvement according to claim 14 wherein the alcohol is benzyl alcohol.

16. The improvement according to claim 14 wherein the alcohol is methanol.

17. The improvement according to claim 14 wherein the alcohol is ethanol.

18. The improvement according to claims 13, 14, 15, 16, or 17 wherein the carbon monoxide pressure is initially between about 1 and 15 atmospheres;
the temperature is between about 20° and 100° C.;
the palladium(II) salt is palladium dichloride;
the copper(II) salt is cupric chloride; and
the nucleophilic base is an alkali or alkaline earth metal salt of a carboxylic acid, said base being employed in an amount corresponding to between about 1 and 4 molar equivalents of copper(II) salt.

19. In the conversion of olefins to carboxylic acids whereby a conjugated diolefin having the formula:

wherein R' and R" are each independently H, saturated alkyl, or aryl and R''' is H or methyl, is carbonylated, by 1,4-addition thereto of carbon monoxide and an alcohol of the formula ROH, to form an unsaturated dicarboxylic ester having the formula:

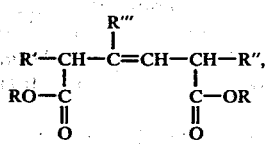

wherein R is benzyl, and said diester is then subjected to catalytic hydrogenation/hydrogenolysis to form a dicarboxylic acid having the formula:

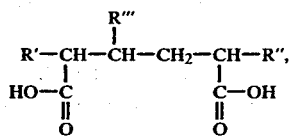

the improvement comprising charging to a reaction vessel the diolefin, a copper(II) salt, a nucleophilic base selected from the group consisting of amines, carbonates, and alkali and alkaline earth metal salts of carboxylic acids, a catalytically effective amount of a palladium(II) salt, and amounts of carbon monoxide and alcohol equal to or greater than the stoichiometric equivalent of diolefin, and subjecting the contents of the charged vessel in the absence of water and oxygen to a carbon monoxide pressure and a temperature sufficient to effect the carbonylation reaction, said process being further characterized in that the amount of copper(II) salt employed is at least sufficient to oxidize the palladium(0) formed in the process back to palladium(II) and the amount of base employed is equal to at least 1 molar equivalent of copper(II) salt.

20. The improvement according to claim 19 wherein the conjugated diolefin is butadiene and the dicarboxylic acid is adipic acid.

21. The improvement according to claim 19 or 20 wherein:
the carbon monoxide pressure is initially between about 1 and 15 atmospheres;
the temperature is between about 20° and 100° C.;
the palladium(II) salt is palladium dichloride;
the copper(II) salt is cupric chloride; and
the nucleophilic base is an alkali or alkaline earth metal salt of a carboxylic acid, said base being employed in an amount corresponding to between 1 and 4 molar equivalents of copper(II) salt.

* * * * *